United States Patent
Kara et al.

(10) Patent No.: US 10,465,220 B2
(45) Date of Patent: Nov. 5, 2019

(54) EXPRESSION PROCESS

(75) Inventors: Bhupendra Vallabh Kara, Billingham (GB); Christopher David John Lennon, Billingham (GB)

(73) Assignee: Fujifilm Diosynth Biotechnologies UK Limited, Billingham (GB)

(*) Notice: Subject to any disclaimer, the term of this patent is extended or adjusted under 35 U.S.C. 154(b) by 201 days.

(21) Appl. No.: 13/883,187

(22) PCT Filed: Nov. 2, 2011

(86) PCT No.: PCT/GB2011/001548
§ 371 (c)(1),
(2), (4) Date: Jun. 12, 2013

(87) PCT Pub. No.: WO2012/059715
PCT Pub. Date: May 10, 2012

(65) Prior Publication Data
US 2014/0370543 A1 Dec. 18, 2014

(30) Foreign Application Priority Data
Nov. 5, 2010 (GB) .................. 1018664.1

(51) Int. Cl.
*C12P 21/00* (2006.01)
*C12N 9/02* (2006.01)
*C12N 9/90* (2006.01)
*C12P 21/02* (2006.01)
*C12N 15/70* (2006.01)

(52) U.S. Cl.
CPC ............ *C12P 21/00* (2013.01); *C12N 9/0051* (2013.01); *C12N 9/90* (2013.01); *C12N 15/70* (2013.01); *C12P 21/02* (2013.01); *C12Y 108/03002* (2013.01); *C07K 2319/02* (2013.01); *C07K 2319/35* (2013.01)

(58) Field of Classification Search
None
See application file for complete search history.

(56) References Cited

U.S. PATENT DOCUMENTS 7,226,781 B1 * 6/2007 Belyaev .............. C07K 14/005 435/320.1

FOREIGN PATENT DOCUMENTS

| WO | WO 98/37208 A1 | 8/1998 | |
| WO | 2004/076669 | 9/2004 | |
| WO | 2008/225596 A2 | 9/2008 | |
| WO | WO 2009147382 A2 * | 12/2009 | ........... C12N 15/625 |
| WO | 2010/139858 | 12/2010 | |

OTHER PUBLICATIONS

Banci et al., PNAS, 2010, vol. 107, pp. 20190-20195.*
Hatahet et al., Microbial Cell Factories, 2010, vol. 9, pp. 1-9.*
Dassa et al., Journal of Bacteriology, 1990, vol. 172, pp. 5497-5500.*
Hell, BBA, 2008, vol. 1783, pp. 601-609.*
Singh et al., Experimental Cell Research, 1997, vol. 234 pp. 205-216.*
Stader et al., "Engineering *Escherichia coli* to Secrete Heterologous Gene Products" 185 Methods in Enzymology 166-187 (1990).*
Goloubinoff et al., "GroE heat-shock proteins promote assembly of foreign prokaryotic ribulose bisphosphate carboxylase oligomers in *Escherichia coli*" 337 Nature 44-47 (1989).*
Hatahet, Disruption of Reducing Pathways is Not Essential for Efficient Disulfide Bond Formation in the Cytoplasm of *E. coli*, Microbial Cell Factories, 9, pp. 1-9, 2010.
Veggiani, Improved Quantitative and Qualitative Production of Single-Domain Intrabodies Mediated by the Co-Expression of Erv1p Sulfhydryl Oxidase, Protein Expression and Purification, 79, pp. 111-114, 2011.
Nguyen, Pre-Expression of Sulfhydryl Oxidase Significantly Increases the Yields of Eukaryotic Disulfide Bond Containing Proteins Expressed in the Cytoplasm of *E. coli*, Microbial Cell Factories, 10, pp. 1-13, 2011.
Banci, Mia40 is an Oxidoreductase that Catalyzes Oxidative Protein Folding in Mitochondria, Nature Structural & Molecular Biology, 16, pp. 198-206, 2009.
Tienson, Reconstitution of the Mia40-Erv1 Oxidative Folding Pathway for the Small Tim Proteins, Molecular Biology of the Cell, 20, pp. 3481-3490, 2009.
Hell, The Erv1-Mia40 Disulfide Relay System in the Intermembrane Space of Mitochondria, Biochimica et Biophysica Acta, 1783, pp. 601-609, 2008.
Hermann, Thiol Oxidation in Bacteria, Mitochondria and Chloroplasts: Common Principles but Three Unrelated Machineries?, Biochimica et Biophysica Acta, 1793, pp. 71-77, 2009.
Lee, Erv1p from *Saccharomyces Cerevisiae* is a FDA-Linked Sulfhydryl Oxidase, FEBS Letters 477, pp. 62-66, 2006.
Koehler et al., "Redox regulation of protein folding in the mitochondrial intermembrane space," Biochimica et Biophysica Acta, 1793: 139-145 (2009).

* cited by examiner

Primary Examiner — Nancy J Leith
(74) Attorney, Agent, or Firm — Morgan, Lewis & Bockius LLP

(57) ABSTRACT

A process for the production of a target recombinant polypeptide is provided. The process comprises expressing an expression cassette encoding the target polypeptide and co-expressing an expression cassette encoding a mitochondrial foldase. Preferred mitochondrial foldases include Mia 40 and Erv1, and homologs thereof.

7 Claims, No Drawings
Specification includes a Sequence Listing.

SEQUENCE LISTING

```
<160> NUMBER OF SEQ ID NOS: 17

<210> SEQ ID NO 1
<211> LENGTH: 141
<212> TYPE: PRT
<213> ORGANISM: Homo sapiens

<400> SEQUENCE: 1

Ser Tyr Ala Arg Gln Glu Gly Lys Asp Arg Ile Ile Phe Val Thr Lys
1               5                   10                  15

Glu Asp His Glu Thr Pro Ser Ser Ala Glu Leu Val Ala Asp Asp Pro
            20                  25                  30

Asn Asp Pro Tyr Glu Glu His Gly Leu Ile Leu Pro Asn Gly Asn Ile
        35                  40                  45

Asn Trp Asn Cys Pro Cys Leu Gly Gly Met Ala Ser Gly Pro Cys Gly
    50                  55                  60

Glu Gln Phe Lys Ser Ala Phe Ser Cys Phe His Tyr Ser Thr Glu Glu
65                  70                  75                  80
```

```
Ile Lys Gly Ser Asp Cys Val Asp Gln Phe Arg Ala Met Gln Glu Cys
                85                  90                  95
Met Gln Lys Tyr Pro Asp Leu Tyr Pro Gln Glu Asp Glu Glu
            100                 105                 110
Glu Glu Arg Glu Lys Lys Pro Ala Glu Gln Ala Glu Thr Ala Pro
        115                 120                 125
Ile Glu Ala Thr Ala Thr Lys Glu Glu Glu Gly Ser Ser
    130                 135                 140

<210> SEQ ID NO 2
<211> LENGTH: 23
<212> TYPE: PRT
<213> ORGANISM: Artificial Sequence
<220> FEATURE:
<223> OTHER INFORMATION: Sequence leader 1

<400> SEQUENCE: 2

Met Lys Val Ser Thr Ala Phe Leu Cys Leu Leu Leu Thr Val Ser Ala
1               5                   10                  15

Phe Ser Ala Gln Val Leu Ala
            20

<210> SEQ ID NO 3
<211> LENGTH: 105
<212> TYPE: PRT
<213> ORGANISM: Escherichia coli

<400> SEQUENCE: 3

Ile Ile His Leu Thr Asp Asp Ser Phe Asp Thr Asp Val Leu Lys Ala
1               5                   10                  15

Asp Gly Ala Ile Leu Val Asp Phe Trp Ala Glu Trp Ser Gly Pro Ser
            20                  25                  30

Lys Met Ile Ala Pro Ile Leu Asp Glu Ile Ala Asp Glu Tyr Gln Gly
        35                  40                  45

Lys Leu Thr Val Ala Lys Leu Asn Ile Asp Gln Asn Pro Gly Thr Ala
    50                  55                  60

Pro Lys Tyr Gly Ile Arg Gly Ile Pro Thr Leu Leu Phe Lys Asn
65                  70                  75                  80

Gly Glu Val Ala Ala Thr Lys Val Gly Ala Leu Ser Lys Gly Gln Leu
                85                  90                  95

Lys Glu Phe Leu Asp Ala Asn Leu Ala
            100                 105

<210> SEQ ID NO 4
<211> LENGTH: 276
<212> TYPE: PRT
<213> ORGANISM: Artificial Sequence
<220> FEATURE:
<223> OTHER INFORMATION: Thioredoxin fusion protein

<400> SEQUENCE: 4

Met Lys Val Ser Thr Ala Phe Leu Cys Leu Leu Leu Thr Val Ser Ala
1               5                   10                  15

Phe Ser Ala Gln Val Leu Ala Asp Tyr Lys Asp Glu Asp Lys Ile Ile
            20                  25                  30

His Leu Thr Asp Asp Ser Phe Asp Thr Asp Val Leu Lys Ala Asp Gly
        35                  40                  45

Ala Ile Leu Val Asp Phe Trp Ala Glu Trp Ser Gly Pro Ser Lys Met
    50                  55                  60
```

Ile Ala Pro Ile Leu Asp Glu Ile Ala Asp Glu Tyr Gln Gly Lys Leu
65                  70                  75                  80

Thr Val Ala Lys Leu Asn Ile Asp Gln Asn Pro Gly Thr Ala Pro Lys
                85                  90                  95

Tyr Gly Ile Arg Gly Ile Pro Thr Leu Leu Leu Phe Lys Asn Gly Glu
            100                 105                 110

Val Ala Ala Thr Lys Val Gly Ala Leu Ser Lys Gly Gln Leu Lys Glu
        115                 120                 125

Phe Leu Asp Ala Asn Leu Ala Ser Tyr Ala Arg Gln Glu Gly Lys Asp
130                 135                 140

Arg Ile Ile Phe Val Thr Lys Glu Asp His Glu Thr Pro Ser Ser Ala
145                 150                 155                 160

Glu Leu Val Ala Asp Asp Pro Asn Asp Pro Tyr Glu Glu His Gly Leu
                165                 170                 175

Ile Leu Pro Asn Gly Asn Ile Asn Trp Asn Cys Pro Cys Leu Gly Gly
            180                 185                 190

Met Ala Ser Gly Pro Cys Gly Glu Gln Phe Lys Ser Ala Phe Ser Cys
        195                 200                 205

Phe His Tyr Ser Thr Glu Glu Ile Lys Gly Ser Asp Cys Val Asp Gln
210                 215                 220

Phe Arg Ala Met Gln Glu Cys Met Gln Lys Tyr Pro Asp Leu Tyr Pro
225                 230                 235                 240

Gln Glu Asp Glu Asp Glu Glu Glu Arg Glu Lys Lys Pro Ala Glu
                245                 250                 255

Gln Ala Glu Glu Thr Ala Pro Ile Glu Ala Thr Ala Thr Lys Glu Glu
            260                 265                 270

Glu Gly Ser Ser
        275

<210> SEQ ID NO 5
<211> LENGTH: 986
<212> TYPE: DNA
<213> ORGANISM: Artificial Sequence
<220> FEATURE:
<223> OTHER INFORMATION: Thioredoxin fusion protein gene

<400> SEQUENCE: 5
gcggccgcga tatcacgcgt ttaggcaccc caggctttac actttatgct tccggctggt      60
atgttgtgtg gactttaaga aggagatata catatgaagg taagcaccgc attttttgtgc    120 ctgttattga cggtcagcgc attcagcgca caagtcctgg cggactataa ggacgaggac     180
aagatcattc acctgaccga tgactcgttc gacaccgacg tgctgaaagc tgatggtgcc    240
atcctggtcg acttctgggc ggagtggagc ggtccgagca agatgattgc gccgatcctg    300
gatgagattg cagatgaata ccagggcaaa ctgacggttg caaaattgaa cattgatcaa    360
aacccgggca cggctccgaa gtatggcatt cgtggtatcc cgaccctgct gctgttcaag    420
aatggtgagg tggcggcgac caaggttggc gcgctgtcca agggtcaact gaaagagttt    480
ctggacgcta atttggcaag ctacgcgcgt caggaaggta agatcgcat tatctttgtt     540 accaaagagg atcatgaaac cccgagcagc gcggagttgt tgcggacga tccgaacgat    600 ccgtacgaag agcatggcct gatcctgccg aatggtaaca tcaattggaa ctgcccgtgc    660
ctgggtggca tggccagcgg tccgtgcggc gagcagttca atcagcatt tagctgtttt    720 cactacagca ctgaagagat caaaggtagc gactgcgtgg accagttccg tgccatgcag    780

```
gagtgtatgc aaaagtatcc agacctgtac cctcaggaag atgaggatga agaagaagag    840
cgcgagaaga aaccggcgga gcaagccgaa gaaacggccc caattgaggc aaccgcgacg    900
aaagaagaag agggttcttc ctaatgaatt atattactaa ttaattgggg accctagagg    960
tccccttttt tattttaaaa ctcgag                                        986
```

```
<210> SEQ ID NO 6
<211> LENGTH: 204
<212> TYPE: PRT
<213> ORGANISM: Homo sapiens

<400> SEQUENCE: 6
```

Ala Ala Pro Gly Glu Arg Gly Arg Phe His Gly Gly Asn Leu Phe Phe
1               5                   10                  15

Leu Pro Gly Gly Ala Arg Ser Glu Met Met Asp Asp Leu Ala Thr Asp
            20                  25                  30

Ala Arg Gly Arg Gly Ala Gly Arg Arg Asp Ala Ala Ala Ser Ala Ser
        35                  40                  45

Thr Pro Ala Gln Ala Pro Thr Ser Asp Ser Pro Val Ala Glu Asp Ala
    50                  55                  60

Ser Arg Arg Arg Pro Cys Arg Ala Cys Val Asp Phe Lys Thr Trp Met
65                  70                  75                  80

Arg Thr Gln Gln Lys Arg Asp Thr Lys Phe Arg Glu Asp Cys Pro Pro
                85                  90                  95

Asp Arg Glu Glu Leu Gly Arg His Ser Trp Ala Val Leu His Thr Leu
            100                 105                 110

Ala Ala Tyr Tyr Pro Asp Leu Pro Thr Pro Glu Gln Gln Gln Asp Met
        115                 120                 125

Ala Gln Phe Ile His Leu Phe Ser Lys Phe Tyr Pro Cys Gly Glu Cys
    130                 135                 140

Ala Glu Asp Leu Arg Lys Arg Leu Cys Arg Asn His Pro Asp Thr Arg
145                 150                 155                 160

Thr Arg Ala Cys Phe Thr Gln Trp Leu Cys His Leu His Asn Glu Val
                165                 170                 175

Asn Arg Lys Leu Gly Lys Pro Asp Phe Asp Cys Ser Lys Val Asp Glu
            180                 185                 190

Arg Trp Arg Asp Gly Trp Lys Asp Gly Ser Cys Asp
        195                 200

```
<210> SEQ ID NO 7
<211> LENGTH: 235
<212> TYPE: PRT
<213> ORGANISM: Artificial Sequence
<220> FEATURE:
<223> OTHER INFORMATION: ALRP fusion protein

<400> SEQUENCE: 7
```

Met Lys Val Ser Thr Ala Phe Leu Cys Leu Leu Leu Thr Val Ser Ala
1               5                   10                  15

Phe Ser Ala Gln Val Leu Ala Asp Tyr Lys Asp Asp Asp Lys Ala
            20                  25                  30

Ala Pro Gly Glu Arg Gly Arg Phe His Gly Gly Asn Leu Phe Phe Leu
        35                  40                  45

Pro Gly Gly Ala Arg Ser Glu Met Met Asp Asp Leu Ala Thr Asp Ala
    50                  55                  60

Arg Gly Arg Gly Ala Gly Arg Arg Asp Ala Ala Ala Ser Ala Ser Thr
65                  70                  75                  80

Pro Ala Gln Ala Pro Thr Ser Asp Ser Pro Val Ala Glu Asp Ala Ser
            85                  90                  95

Arg Arg Arg Pro Cys Arg Ala Cys Val Asp Phe Lys Thr Trp Met Arg
            100                 105                 110

Thr Gln Gln Lys Arg Asp Thr Lys Phe Arg Glu Asp Cys Pro Pro Asp
            115                 120                 125

Arg Glu Glu Leu Gly Arg His Ser Trp Ala Val Leu His Thr Leu Ala
            130                 135                 140

Ala Tyr Tyr Pro Asp Leu Pro Thr Pro Glu Gln Gln Gln Asp Met Ala
145                 150                 155                 160

Gln Phe Ile His Leu Phe Ser Lys Phe Tyr Pro Cys Glu Glu Cys Ala
                165                 170                 175

Glu Asp Leu Arg Lys Arg Leu Cys Arg Asn His Pro Asp Thr Arg Thr
            180                 185                 190

Arg Ala Cys Phe Thr Gln Trp Leu Cys His Leu His Asn Glu Val Asn
            195                 200                 205

Arg Lys Leu Gly Lys Pro Asp Phe Asp Cys Ser Lys Val Asp Glu Arg
210                 215                 220

Trp Arg Asp Gly Trp Lys Asp Gly Ser Cys Asp
225                 230                 235

<210> SEQ ID NO 8
<211> LENGTH: 861
<212> TYPE: DNA
<213> ORGANISM: Artificial Sequence
<220> FEATURE:
<223> OTHER INFORMATION: ALRP fusion protein gene

<400> SEQUENCE: 8
gatatcacgc gtttaggcac cccaggcttt acactttatg cttccggctg gtatgttgtg      60
tggactttaa gaaggagata catatatgaa agtgagcacc gcattcttgt gtctgctgtt     120
gacggtctcc gcgttcagcg cacaagtttt ggcggactat aaggatgacg atgacaaagc     180
ggcaccgggc gaacgcgtc gtttccacgg tggcaatttg ttttcctgc cgggcggcgc      240 ccgcagcgag atgatggacg acttggcgac tgacgcgcgt ggtcgtggtg ctggtcgtcg     300
tgatgcagcg gcctcggcaa gcacgccggc tcaggcccca acctccgata gcccggtggc     360
ggaggacgct agccgccgtc gcccgtgtcg tgcgtgtgtt gactttaaaa cctggatgcg     420
tacccaacag aagcgtgaca ccaagtttcg cgaagactgc ccgccggacc gtgaggaact     480
gggtcgccac tcttgggcgg tcctgcacac gctggcggcg tactacccgg atctgcctac     540
gccggaacag cagcaggata tggcgcaatt catccatctg tttagcaagt tttatccttg     600
cgaggagtgt gccgaagatt tgcgtaagcg cctgtgtcgt aaccatccgg acacccgtac     660
ccgtgcctgc tttacccaat ggttgtgcca cctgcacaat gaagttaacc gcaaattggg     720
caaaccggat ttcgactgca gcaaagtgga tgagcgttgg cgtgatggtt ggaaggatgg     780
tagctgcgat taatgaatta tattactaat taattgggga ccctagaggt ccccttttt      840 attttaaaac tcgaggatat c                                                861

<210> SEQ ID NO 9
<211> LENGTH: 300
<212> TYPE: DNA
<213> ORGANISM: Artificial Sequence
<220> FEATURE:
<223> OTHER INFORMATION: IGF plus leader gene

<400> SEQUENCE: 9

```
catatgatga ttaccctgcg taaactgccg ctggcagtcg cagttgcagc cggtgttatg    60
agcgcacagg caatggcagg tccggaaacc ctgtgtggtg cagaactggt tgatgcactg   120
cagtttgttt gtggtgatcg tggcttttat tttaataaac cgaccggtta tggtagcagc   180
agccgtcgtg cacgtcagac cggtattgtt gatgaatgtt gctttcgtag ctgtgatctg   240
cgtcgtctgg aaatgtattg tgcaccgctg aaaccggcaa aaagcgcata taactcgag    300
```

<210> SEQ ID NO 10
<211> LENGTH: 651
<212> TYPE: DNA
<213> ORGANISM: Artificial Sequence
<220> FEATURE:
<223> OTHER INFORMATION: hGH plus leader gene

<400> SEQUENCE: 10

```
catatgaaaa agactgctat tgctattgcg gttgctctgg ctggtttcgc caccgtggcg    60
caggcattcc cgacgattcc gctgtctcgt ctgttcgata cgctatgct gcgtgcacat   120
cgtctgcacc agctggcatt cgacacttat caagaattcg aggaggccta catcccgaaa   180
gaacagaaat acagcttcct gcagaacccg caaacctccc tgtgcttcag cgaatccatc   240
ccgactccgt ctaaccgcga agaaacccag cagaaatcta atctggaact gctgcgtatt   300
agcctgctgc tgatccagtc ttggctggaa ccggtgcaat tcctgcgcag cgtcttcgcg   360
aactccctgg tatatggcgc ttccgactct aacgtatacg atctgctgaa agacctggag   420
gagggtatcc agaccctgat gggccgcctg gaggacggca gccgcgtac tggccagatc   480
tttaaacaga cttactctaa attcgacacc aactcccata tgatgacgc cctgctgaaa   540
aactatggtc tgctgtactg cttccgtaaa gacatggaca agttgagac cttcctgcgt   600
attgttcagt gtcgctctgt tgagggttct tgcggcttct aatgactcga g            651
```

<210> SEQ ID NO 11
<211> LENGTH: 1551
<212> TYPE: DNA
<213> ORGANISM: Artificial Sequence
<220> FEATURE:
<223> OTHER INFORMATION: A5B7 Fab gene

<400> SEQUENCE: 11

```
catatgaaga agactgctat tgctattgcg gttgcactgg ctggtttcgc taccgtggcg    60
caggcacagg ttcagctgca ggaaagcggc ggtggtctgg ttcagccagg cggtagcctg   120
cgtctgtcct gcgctaccag cggtttcact tttaccgact actacatgaa ctgggtgcgt   180
cagccgccag caaaagcgct ggaatggctg ggcttcatcg gtaacaaagc taacggctac   240
actaccgagt actccgcatc tgtaaaaggt cgttttacca tctctcgtga caaaagccag   300
tctatcctgt acctgcagat gaataccctg cgcgctgaag actccgcgac ttattactgt   360
acccgtgacc gtggtctgcg ttttacttc gactactggg gtcagggtac cactgtaacg   420
gtcagctccg cctccactaa aggcccgagc gtatttcctc tggcgccgtc ctccaagtcc   480
actagcggcg gcaccgcagc tctgggctgt ctggttaaag actacttccc agagccggtg   540
accgtttcct ggaacagcgg tgcactgacc agcggcgttc acacgtttcc ggccgtgctg   600
caatcctccg gtctgtactc tctgtcttcc gtcgtcaccg ttccgtctag ctctctgggc   660
actcagacct atatctgcaa cgtcaatcac aaacccgtcta acaccaaagt tgacaagaaa   720
gtggagccga atcttgcga taaaacgcac acctaataac tggccctgag ctccaagttc   780
```

```
tactttaaag aaacggttat catgaaaaag accgccatcg ctatcgctgt tgcgctggca      840
ggctttgcta cggttgctca agctgacatc gaactgtctc agtctccggc gatcctgtcc      900
gcgtctccag gcgaaaaagt aactatgacc tgtcgcgcta gctcttccgt tacctacatc      960
cactggtatc agcagaaacc gggttcttcc ccgaaaagct ggatctacgc aacctccaac     1020
ctggcttccg gcgttccggc tcgttttttct ggttctggct ctggcacgtc ctattctctg    1080
accatcagcc gtgtagaggc agaagacgca gctacctatt actgccagca ctggtcctcc    1140
aaacctccga ctttcggtgg cggcaccaaa ctggaaatca gcgtaccgt cgccgctccg     1200
tctgttttca ttttcccgcc gtccgacgag cagctgaaat ccggtaccgc cagcgtagtg    1260
tgcctgctga acaacttcta cccacgtgag gctaaagttc agtggaaagt ggacaatgcc    1320
ctgcagagcg gcaactccca ggaatccgtt accgaacagg acagcaaaga ttccacttat    1380
tccctgtctt ccactctgac tctgagcaaa gcagattacg agaagcataa ggtgtacgcc    1440
tgtgaagtga ctcaccaggg tctgtcctct ccggttacga aaagctttaa ccgtggcgag    1500
tgctaataag gatccagctc gaattccatc gatgatatca gatctctcga g              1551

<210> SEQ ID NO 12
<211> LENGTH: 621
<212> TYPE: DNA
<213> ORGANISM: Artificial Sequence
<220> FEATURE:
<223> OTHER INFORMATION: FGF21 plus leader gene

<400> SEQUENCE: 12
catatgaaaa aaccgctat tgcaattgca gttgcactgg caggttttgc aaccgttgca      60
caggcacatc cgattccgga tagcagtccg ctgctgcagt ttggtggtca ggttcgtcag    120
cgttatctgt ataccgatga tgcacagcag accgaagcac atctggaaat tcgtgaagat    180
ggcaccgttg gtggtgcagc agatcagagt ccggaaagcc tgctgcagct gaaagcactg    240
aaaccgggtg ttattcagat tctgggtgtt aaaaccagcc gttttctgtg tcagcgtccg    300
gatggtgcac tgtatggtag cctgcatttt gatccggaag catgtagctt tcgtgaactg    360
ctgctggaag atggttataa tgtttatcag agcgaacatc atggtctgcc actgcatctg    420
cctggtaata aaagtccgca tcgtgatccg gcaccgcgtg gtccggcacg ttttctgccg    480
ctgcctggtc tgcctcctgc actgccggaa cctccgggta ttctggcacc gcagcctccg    540
gatgttggta gcagcgatcc gctgagcatg gttggtccga gccagggtcg tagcccgagc    600
tatgcaagct ataactcga g                                                621

<210> SEQ ID NO 13
<211> LENGTH: 488
<212> TYPE: DNA
<213> ORGANISM: Artificial Sequence
<220> FEATURE:
<223> OTHER INFORMATION: RapLR plus leader gene

<400> SEQUENCE: 13
gaaggccgtc aaggccacgt gtcttgtcca ggtaccatat gaaaaaaacc gccattgcaa      60
ttgcagttgc tctggcaggt tttgcaaccg ttgcacaggc acaggattgg ctgacctttc    120
agaaaaaaca tctgaccaat acccgtgatg tggattgcaa taatattatg agcaccaacc    180
tgtttcattg caaagataaa aataccctta tttatagccg tccggaaccg gttaaagcaa    240
tttgtaaagg tattattgcc agcaaaaatg tgctgaccac gagcgagttt atctgagcg     300
```

```
attgtaatgt taccagccgt ccgtgtaaat ataaactgaa aaaaagcacc aatacctttt    360
gcgtgacctg tgaaaatcag gcaccggttc attttgttgg tgttggtcat tgtgaacaga    420
aactgattag cgaagaagat ctgtaataac tcgagctctg gagcacaaga ctggcctcat    480
gggccttc                                                              488

<210> SEQ ID NO 14
<211> LENGTH: 279
<212> TYPE: DNA
<213> ORGANISM: Artificial Sequence
<220> FEATURE:
<223> OTHER INFORMATION: Elafin plus leader gene

<400> SEQUENCE: 14
catatgaaaa aaaccgccat tgcaattgca gttgctctgg caggttttgc aaccgttgca     60
caggcagcac aggaaccggt taaaggtccg gttagcacca aaccgggtag ctgtccgatt    120
attctgattc gttgtgcaat gctgaatcct ccgaatcgtt gtctgaaaga taccgattgt    180
ccgggtatta aaaatgttg tgaaggtagc tgtggcatgg catgttttgt tccgcaggaa    240
cagaaactga ttagcgaaga agatctgtaa taactcgag                           279

<210> SEQ ID NO 15
<211> LENGTH: 1152
<212> TYPE: DNA
<213> ORGANISM: Artificial Sequence
<220> FEATURE:
<223> OTHER INFORMATION: MIC6 plus leader gene

<400> SEQUENCE: 15
catatgaaaa aaaccgccat tgcaattgca gttgctctgg caggttttgc aaccgttgca     60
caggcacgtc tgtttcgttg ttgtgcagca gcagttgttg cagcagaaag cctgctgtgg    120
ctgaaaaatg gtagcccgtt ttttgcattt ctgcctggta atggtgaaat tgcagataat    180
tgtagcggta atccgtgtgg tggcaccgca gcaggcacct gtattaatac cccgagcggt    240
tatgattgtc gttgtgaacc gggttatgtt ctgggtgttg aaaatgatca ggttacctgt    300
atgatgccga gcggtgttcc gatggcaaat tttgttcagc tgagcgaaaa accggcagca    360
tgtagcagca atccgtgcgg tccggaagca gcaggtacat gtaatgaaac caatagcggt    420
tatatttgcc gttgcaatca gggttatcgt attagcctgg atggcaccgg taatgttacc    480
tgtattgttc gtcaggaaag cggttgcgaa gaaaatggtt gtggtccgcc ggatgccgtt    540
cagagctgtc gtcgtctgac cggcacagca ggtcgtctgt gtgtttgtaa agaaaatttt    600
attgccacca ttgatgccag cgcacatatt acctgtaaac gtgttccgcc gcattatcgt    660
aaaccgccgt ttgaatttgg taaaggtggt catccggttg atagcgaacc gagcaaacgt    720
cagcgtgaag atgaaggtga aagccgtgaa ccggaaagcg atagcaccga accgggtcgt    780
gatcaggaac gtcgtacacc gctggaagaa agccaggaac cggaaggtag cacaccggat    840
agccagcaga gccgtggtgg tagcggtagc gatagtaccg aaagcgaaga acagggtaaa    900
gaacgtgaag aaggtagcgg tcacgccggt gcaattgccg tggtgttat tggtggtctg    960 ctgctgctga gcgcagccgg tgccggtgtt gcatatatgc gtaaaagcgg tagcggtggt   1020
ggtgaagaaa ttgaatatga acgtggtatt gaagcagcag aagcaagcga agttgaagtt   1080
ctggttgatc tggatagcaa aacctgggat gaacagaaac tgattagcga agaagatctg   1140
taataactcg ag                                                       1152
```

```
<210> SEQ ID NO 16
<211> LENGTH: 7
<212> TYPE: PRT
<213> ORGANISM: Artificial Sequence
<220> FEATURE:
<223> OTHER INFORMATION: Tag

<400> SEQUENCE: 16

Asp Tyr Lys Asp Glu Asp Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Tag

<400> SEQUENCE: 17

Asp Tyr Lys Asp Asp Asp Asp Lys
1               5
```

EXPRESSION PROCESS

SEQUENCE LISTING SUBMISSION VIA EFS-WEB

A computer readable text file, entitled "056258-5145_SequenceListing.txt," created on or about 2 May 2013, with a file size of about 20 kb contains the sequence listing for this application and is hereby incorporated by reference in its entirety.

The present invention concerns a process for expressing recombinant polypeptides.

The manufacture of polypeptides by recombinant technology has proven to be an effective and versatile method, especially when the host organism is *E. coli*. Recombinant polypeptides produced by the host cell can be retained in the cytoplasm, for example as insoluble inclusion bodies, or can be secreted into the periplasm or into the culture medium for the cell. Whilst there are certain advantages to the retention of polypeptides in the cytoplasm, such polypeptides are often expressed in an inactive form. Thus, complex refolding methods must be employed in order to convert the polypeptide to an active, correctly-folded form. Proteins secreted into the periplasm or culture medium are often more readily converted to the correct form and may be obtained more easily in greater yields.

Methods of achieving increased secretion into the periplasm are well know in the art, and include the use of so-called secretion leaders, also know as signal peptide sequences. Such secretion leaders include native host cell systems, such as the spA, phoA, ribose binding protein, pelB, ompA, ompT, dsbA, torA, torT, and tolT leaders in *E. coli* and eukaryotic leader sequences, such as those disclosed in WO 2009/147382. U.S. Pat. No. 5,639,635 discloses that DsbA and DsbC proteins can be employed to improve secretion and correct folding of recombinant polypeptides. It remains desirable to identify further methods for facilitating the secretion of recombinant polypeptides.

According to the present invention, there is provided a process for the production of a target recombinant polypeptide which comprises expressing an expression cassette encoding the target polypeptide and co-expressing an expression cassette encoding a mitochondrial foldase.

Mitochondrial foldases are a class of proteins which function in the formation of disulphide bonds and the correct folding of proteins in the inter-membrane space of mitochondria. Mitochondrial foldases which can be employed in the process of the present invention include mitochondrial sulphydryl oxidases. Mitochondrial foldases which can be employed include insect and plant mitochondrial foldases, and especially mammalian and yeast mitochondrial foldases, and functional fragments of any of the foregoing. Functional fragments of mitochondrial foldases commonly include the sulphydryl oxidase domain fragment of the corresponding reference foldase or homologs thereof having sulphydryl oxidase activity. For example, yeast mitochondrial foldases commonly comprise a sequence serving to anchor the active motif to the mitochondrial membrane. In the present invention, the yeast mitochondrial foldase may be employed with the anchoring sequence present, or the anchor sequence may be omitted.

Examples of mitochondrial foldases are members of the Mia40 family and homologs thereof and members of the Erv family, especially the Erv1 and Erv2 families and homologs thereof.

Members of the Mia 40 family which can be employed include the homologs of Mia40 from *Danio rerio, Xenopus laevis, Gallus gallus, Homo sapiens, Mus musculus, Rattus norvegicus, Canis lupus familiaris, Equus cabbalus, Cricetulus griseus, Strogylocentratus purpuratus, Apis mellifera, Drosophila melanogaster, Culex pipiens, Neurosporasa crassa, Aspergillus niger, Aspergillus clavatus, Aspergillus furnigatus, Saccharomyces cerevisiae, Candida albicans, Candida glabrata, Ashbya gossypil, Cryptococcus neoformans, Pichia pastoris, Hansenula polymorpha, Ostreococcus tauri, Populus trichocarpa, Arabidopsis thaliana* and *Dictyostelium discoideum*, preferably *Homo sapiens* and *Saccharomyces cerevisiae*. In certain embodiments, homologs of Mia 40 that can be employed have greater than 40%, often greater than 50%, commonly greater than 60% homology, preferably greater than 80% homology, most preferably greater than 90%, especially greater than 95%, homology with Sequence ID No.1, below. A preferred homolog of Mia40 is Human Coiled Coil Helix Coiled Coil Helix Domain containing protein-4 (CHCHD-4) having Sequence ID No.1.

Members of the Erv family which can be employed include the homologs of Erv 1 and Erv 2 derived from yeasts, mammals, insects and plants. Members of the erv family which can be employed include those from *Danio rerio, Xenopus laevis, Gallus gallus, Homo sapiens, Mus musculus, Rattus norvegicus, Canis lupus familiaris, Equus cabbalus, Cricetulus griseus, Strogylocentratus purpuratus, Apis mellifera, Drosophila melanogaster, Culex pipiens, Neurosporasa crassa, Aspergillus niger, Aspergillus clavatus, Aspergillus furnigatus, Saccharomyces cerevisiae, Candida albicans, Candida glabrata, Ashbya gossypil, Cryptococcus neoformans, Pichia pastoris, Hansenula polymorpha, Ostreococcus tauri, Populus trichocarpa, Arabidopsis thaliana, Dictyostelium discoideum. Solanum tuberosam, Vitis vinifera, Medicato truncatula, Glycine max, Hordeum vulgare, Sorghum bicolour* and *Zea mays*, preferably *Homo sapiens* and *Saccharomyces cerevisiae*.

In certain embodiments, the homologs of Ent, such as Erv1 and Erv2 comprise a sulphydryl oxidase region comprising the redox centre, a pair of cysteines separated by two amino acids (a —CXXC— motif) and a pair of cysteines separated by 16 amino acids (a C-16-C motif) and a flavin adenine dinucleotide (FAD) binding site.

In some preferred embodiments, an Erv1 homolog is employed comprising a sulphydryl oxidase region having at least 40% homology preferably greater than 80% homology, most preferably greater than 90%, especially greater than 95% homology with amino acids 74 to 173 of Sequence ID No. 6.

In some embodiments, homologs of Erv1 that can be employed have greater than 40%, often greater than 50%, commonly greater than 60% homology, preferably greater than 80% homology, most preferably greater than 90%, especially greater than 95%, homology with Sequence ID No.6, below. A preferred homolog of Erv1 is Human Augmenter of Liver Regeneration Protein (ALRP) having Sequence ID No.6.

In certain embodiments, the mitochondrial foldase employed is a functional fragment of erv1 or erv2, especially plant, yeast or human erv1 or erv2, comprising the redox centre, a pair of cysteines separated by two amino acids (a —CXXC— motif) and a pair of cysteines separated by 16 amino acids (a C-16-C motif) and an FAD binding site, for example a fragment comprising from 80 to 120 amino acids, commonly from 90 to 110 amino acids, and especially about 100 amino acids.

One or more mitochondrial foldases may be co-expressed with the target polypeptide, preferably two or more, and especially a member of the Mia40 family and a member of the erv1 or erv2 families.

In many preferred embodiments, the mitochondrial foldase is expressed with a secretion leader, preferably attached to the N-terminus of the foldase. In certain embodiments, the foldase comprises an N-terminal tag, the secretion leader being attached to the tag, preferably to the N-terminus of the tag. Examples of sequence leaders which can be employed include spA, phoA, ribose binding protein, pelB, ompA, ompT, dsbA, torA, torT, and tolT leaders in E. coli and eukaryotic leader sequences SEQ ID Numbers 1, 2, 3, 4 and 5 disclosed in WO 2009/147382. Where two or more foldases are expressed, the sequence leaders employed may be the same or different. Combinations of sequence leader and foldase are commonly identified by screening combinations by methods well known to those skilled in the art, and selecting the combination offering the desired properties. The secretion leaders employed achieve transfer of foldase to the periplasm.

In certain embodiments, the mitochondrial foldase, especially members of the Mia40 family, is expressed with a solubility fusion partner to increase solubility of the foldase in the periplasm. Examples of solubility fusion partners are well know in the art. A preferred solubility fusion partner is thioredoxin, which may be employed in either active or an inactivated form.

Expression of the mitochondrial foldase and the target polypeptide is under the control of promoters, which may be either constitutive or inducible. In certain embodiments, expression of the mitochondrial foldase is under the control of a constitutive promoter, and expression of the target polypeptide is under the control of an inducible promoter. In other embodiments, the expression of both the mitochondrial foldase and the target polypeptide is under the control of inducible promoters. In these embodiments, the inducible promoters may be controlled by the same inducer, or by different inducers. It will be recognised that the inducible promoters may be the same or different. In some embodiments, the mitochondrial foldase and the target polypeptide are under the control of a single promoter, preferably an inducible promoter.

Where two or more mitochondrial foldases are co-expressed, the same type of promoter or different promoters may be employed with each foldase. Expression of each foldase may be under the control of a single promoter if desired.

In many preferred embodiments, the promoter is a prokaryotic promoter. Examples of prokaryotic promoters that can be employed include:
  a) phage RNA polymerase-dependent promoters, particularly T7 RNA polymerase-dependent promoter systems, preferably single T7 promoters, including those disclosed by Studier and Moffat, J. Mol. Biol. 189;113-130 (1986), incorporated herein by reference, especially a T7 gene 10 promoter; and
  b) host RNA polymerase-based promoter systems, especially E. coli RNA polymerase-based promoter systems.

When a T7 RNA-polymerase dependent promoter system is employed, it will be recognised that a source of 17 RNA polymerase is required, which is provided by methods known in the art, and commonly by inserting a λDE3 prophage expressing the required phage polymerase into the host strain to create lysogenic host strains. The 17 RNA polymerase can also be delivered to the cell by infection with a specialised λ transducing phage that carries the gene for the T7 RNA polymerase.

Examples of constitutive promoters which can be employed in aspects of the present invention include T7A1, T7A2, T7A3, spc ribosomal protein operon promoter, β-lactamase gene promoter, $P_L$ promoter of phage λ, replication control promoters $P_{RNAI}$ and $P_{RNAII}$, P1 and P2 promoter of the rrnB ribosomal RNA operon, Lac repressor protein promoter pLacl, glyceraldehyde phosphate dehydrogenase (GAPDH) and plasma membrane H(+)-ATPase (PMA1) promoter, mating factor (MF)-α promoter, KEX2, TEF-1, simian virus 40 (SV40) early promoter, rous sarcoma virus (RSV) promoter, cytomegalovirus (CMV) promoter, and human β-actin promoter. Further examples of constitutive promoters include inducible promoters which have been modified to remove the control region, for example lac or tac promoters modified to remove the lac or tac operators.

Examples of inducible promoters which can be employed include lac, lacUV5, trp, tac, trc, phoA, arabinose inducible promoters, temperature inducible promoters (both high and low temperature), copper inducible promoters, uspA, uspB, malK, osmotic pressure-inducible promoters, galactose inducible promoters, pheromone inducible promoters, glucoamylase promoter, tetracycline responsive promoters, human c-fos promoter, ecdysone-inducible promoter, and glucocorticoid-inducible promoters.

It will be recognised that promoters are generally selected from promoters known to be effective in the host cell. For example, E. coil promoters are commonly employed in E. coli host cells.

Examples of preferred promoters, either employed in constitutive or inducible forms, include T7 gene 10 promoter, T7A1, T7A2, T7A3, λpL, λpR, lac, lacUV5, trp, tac, trc, ara, phoA and rrnB. Most preferred promoters are λpL, lac and tac.

The expression cassettes employed in the process of the present invention are comprised within expression vectors. Expression vectors may be integrated into the host cell genome, but are preferably comprised within an extrachromosomal element such as a plasmid. Alternatively, the expression vector may be incorporated into phage or viral vectors and these used to deliver the expression system into the host cell system. The expression vectors can be assembled by methods known in the art.

The expression vector of the present invention is commonly employed in the form of a plasmid. The plasmids may be extrachromosomal plasmids or integrative plasmids, preferably extrachromosomal plasmids.

Expression vectors comprising inducible promoters commonly comprise an operator sequence. Operator sequences which may be employed in the process according to the present invention include lac, gal, deo and gln. One or more perfect palindrome operator sequences may be employed. In some embodiments, two perfect palindrome operator sequences are employed, most advantageously one operator sequence being located downstream of the promoter, and one operator sequence being located upstream of the promoter. When two operator systems are employed, the operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point.

It will be recognised that the operator system is commonly employed with an appropriate repressor sequence.

Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid.

The expression vector, particularly when the vector comprises a plasmid, typically also comprises one or more of the following: a selectable marker, for example a sequence conferring antibiotic resistance, and a cer stability sequence.

Host cells which can be employed in the process of the present invention are prokaryotic host cells. Examples of prokaryotic cells include bacterial cells, for example gram-negative bacterial cells, including *E. coli, Salmonella typhimurium, Serratia marsescens, Pseudomonas putida* and *Pseudomonas aeruginosa*, and gram-positive bacterial cells including *Bacillus subtilis*. Preferred host cells are bacteria, particularly enterobacteriacae, preferably *E coli*, and especially B or K12 strains thereof.

In many particularly preferred embodiments, the target polypeptide is expressed with a secretion leader, especially a periplasmic secretion leader to achieve secretion into the periplasm, preferably attached to the N-terminus of the polypeptide. In some embodiments, the target polypeptide comprises an N-terminal tag, the secretion leader being attached to the tag, preferably to the N-terminus of the tag.

Examples of sequence leaders which can be employed include spA, phoA, ribose binding protein, pelB, ompA, ompT, dsbA, torA, torT, and tolT leaders in *E. coli* and eukaryotic leader sequences SEQ ID Numbers 1, 2, 3, 4 and 5 disclosed in WO 2009/147382. The sequence leader employed may be the same as or different from any sequence leader employed with the mitochondrial foldase.

Polypeptides which can be expressed by the process of the present invention include therapeutic proteins and peptides, including cytokines, growth factors, antibodies, antibody fragments, immunoglobulin like polypeptides, enzymes, vaccines, peptide hormones, such as insulins, chemokines, receptors, receptor fragments, kinases, phosphatases, isomerases, hydrolyases, transcription factors and fusion polypeptides.

Antibodies which can be expressed include monoclonal antibodies, polyclonal antibodies and antibody fragments having biological activity, including multivalent and/or multispecific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Preferred antibody fragments that can be prepared are mammalian single variable domain antibodies, being an antibody fragment comprising a folded polypeptide domain which comprises sequences characteristic of immunoglobulin variable domains and which specifically binds an antigen (i.e., dissociation constant of 500 nM or less, such as 400 nM or less, preferably 250 nM or less, and most preferably 100 nM or less), and which binds antigen as a single variable domain; that is, without any complementary variable domain. Single variable domain antibodies include complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains. Preferred single variable domains which can be prepared are selected from the group of $V_H$ and $V_L$, including Vkappa and Vlambda. Most preferably the single variable domains are human or camelid domains, including humanised camelid domains.

Where the target polypeptide comprises two or more chains to be secreted, particularly where the target polypeptide is a fragment antibody comprising two or more chains, each of the chains may be attached to a secretion leader and polynucleotides encoding such polypeptides are designed accordingly. The secretion leaders employed may be the same or different.

The expression system is expressed by methods well known in the art for the cells employed. Preferred expression methods include culturing the host cells in growth medium, especially by fermentation, and then recovering the expressed polypeptide. The term "growth medium" refers to a nutrient medium used for growing the host cells. In many embodiments, a nutrient solution is employed. Suitable growth media for given host cells and methods of recovering polypeptides are well known in the art.

When an inducible promoter is employed, expression may be induced by the addition of an appropriate inducer for such promoter, such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination.

The polypeptide produced by the process of the present invention may be subjected to further purification steps if desired, for example one or more of ion exchange chromatography; chromatography based on hydrophobicity, such as HIC, reverse phase chromatography, hydrophobic charge induction chromatography, or mixed mode chromatography; or size-based purifications such as gel filtration. The polypeptide produced may also be subjected to one or more refolding steps.

Protein expression systems comprising expression cassettes as described above for the co-expression of a mitochondrial foldase and a target polypeptide form another aspect of the present invention. Host cells transformed with such a protein expression system form a further aspect of the present invention. Vectors comprising an expression cassette for a mitochondrial foldase comprise yet a further aspect of the present invention.

The present invention is illustrated without limitation by the following examples.

Summary of polypeptides, vectors and strains

| Polypeptide | Plasmid | Strain minus Foldase | Strain plus Foldase (Plasmid pAVE354) |
|---|---|---|---|
| IGF-1 | pAVE314 | CLD331 | CLD420 |
| D1.3 | pAVE046 | CLD048 | CLD426 |
| A5B7 | pAVE157 | CLD430 | CLD428 |
| hGH | pAVE356 | CLD429 | CLD433 |
| RapLR | pAVE364 | CLD442 | CLD443 |
| Elafin | pAVE362 | CLD438 | CLD439 |
| MIC6 | pAVE363 | CLD440 | CLD441 |
| FGF | pAVE366 | CLD453 | CLD454 |

Construction of pAVE354

The starting plasmid for construction of pAVE354 was pACYCDuet (EMD Biosciences catalogue number 71147-3). The T7 promoters and multiple cloning sites were removed from this vector by digestion with NcoI and XhoI. They were replaced with the NcoI-XhoI fragment of pAVE029 prepared as described in International patent application WO 2007/088371. The resultant plasmid was called NBJ0738-7-3 and confirmed by restriction digest and sequencing.

The protein sequence for the mitochondrial foldase Human Coiled Coil Helix Coiled Coil Helix Domain containing protein-4 (CHCHD-4) protein (a Mia 40 family polypeptide) was obtained from Genbank, accession number AAH33775.1, (Sequence ID No. 1: SYARQEGKDRI-IFVTKEDHETPSSAELVADDPNDPYEEHGLILPNGN-INWNCPCLGGMASGPCGEQFKSAFSCFHYSTEEI KGSDCVDQFRAMQECMQKYPDLYPQEDEDEEEER-EKKPAEQAEETAPIEATATKEEEGSS). A Fusion protein was designed with a secretion leader (Sequence ID No.2: MKVSTAFLCLLLTVSAFSAQVLA). This was attached via a tag (DYKDEDK—Sequence ID No. 16) at the N-terminal of *Escherichia coli* Thioredoxin A (TrxA: Genbank accession number AAA67582.1 (Sequence ID No.3 IIHLTDDSFDTDVLKADGAILVDFWAEWSGPSKMI-APILDEIADEYQGKLTVAKLNIDQNPGTAPKYGIR-GIPTLLLFKNGEVAATKVGALSKGQLKEFLDANLA). The Thioredoxin active site 51CGPC54 was changed to 51SGPS54. The thioredoxin C terminal was fused to the N terminal of CHCHD-4, which was also mutated to remove the non catalytic Cysteine reside at position 3 and replace it with a serine residue. The protein sequence of this fusion protein, including the leader is shown in Sequence ID No.4.

Sequence ID No. 4
MKVSTAFLCLLLTVSAFSAQVLADYKDEDKIIHLTDDSFDTDVLKA

DGAILVDFWAEWSGPSKMIAPILDEIADEYQGKLTVAKLNIDQNPG

TAPKYGIRGIPTLLLFKNGEVAATKVGALSKGQLKEFLDANLASYA

RQEGKDRIIFVTKEDHETPSSAELVADDPNDPYEEHGLILPNGNIN

WNCPCLGGMASGPCGEQFKSAFSCFHYSTEEIKGSDCVDQFRAMQE

CMQKYPDLYPQEDEDEEEEREKKPAEQAEETAPIEATATKEEEGSS

A gene coding for this protein, of Sequence ID No. 5, was cloned into the NdeI/XhoI sites of NBJ0738-7-3 to make NBJ0829-18-3 and confirmed by restriction digest and sequencing.

Sequence ID No. 5
GCGGCCGCGATATCACGCGTTTAGGCACCCCAGGCTTTACACTTTA

TGCTTCCGGCTGGTATGTTGTGTGGACTTTAAGAAGGAGATATACA

TATGAAGGTAAGCACCGCATTTTTGTGCCTGTTATTGACGGTCAGC

GCATTCAGCGCACAAGTCCTGGCGGACTATAAGGACGAGGACAAGA

TCATTCACCTGACCGATGACTCGTTCGACACCGACGTGCTGAAAGC

TGATGGTGCCATCCTGGTCGACTTCTGGGCGGAGTGGAGCGGTCCG

AGCAAGATGATTGCGCCGATCCTGGATGAGATTGCAGATGAATACC

AGGGCAAACTGACGGTTGCAAAATTGAACATTGATCAAACCCGGG

CACGGCTCCGAAGTATGGCATTCGTGGTATCCCGACCCTGCTGCTG

TTCAAGAATGGTGAGGTGGCGGCGACCAAGGTTGGCGCGCTGTCCA

AGGGTCAACTGAAAGAGTTTCTGGACGCTAATTTGGCAAGCTACGC

GCGTCAGGAAGGTAAAGATCGCATTATCTTTGTTACCAAAGAGGAT

CATGAAACCCCGAGCAGCGCGGAGTTGGTTGCGGACGATCCGAACG

ATCCGTACGAAGAGCATGGCCTGATCCTGCCGAATGGTAACATCAA

TTGGAACTGCCCCGTGCCTGGGTGGCATGGCCAGCGGTCCGTGCGGC

GAGCAGTTCAAATCAGCATTTAGCTGTTTTCACTACAGCACTGAAG

AGATCAAAGGTAGCGACTGCGTGGACCAGTTCCGTGCCATGCAGGA

GTGTATGCAAAAGTATCCAGACCTGTACCCTCAGGAAGATGAGGAT

GAAGAAGAAGAGCGCGAGAAGAAACCGGCGGAGCAAGCCGAAGAA

CGGCCCCAATTGAGGCAACCGCGACGAAAGAAGAAGAGGGTTCTTC

CTAATGAATTATATTACTAATTAATTGGGGACCCTAGAGGTCCCCT

TTTTTATTTTAAAACTCGAG

The protein sequence for the mitochondrial foldase Human Augmenter of Liver Regeneration Protein (ALRP, an Ery 1 family polypeptide) was obtained from Genbank accession number EAW85580.1 (Sequence ID No.6: AAPGERGRFHGGNLFFLPGG ARSEMMDDLATDAR-GRGAGRRDAAASASTPAQAPTSDSPVAEDASRRRP-CRACVDFKTWMRTQQKRDTKFREDCPPDREELGRH-SWAVLHTLAAYYPDLPTPEQQQDMAQFIHLFSKFY-PCEECAEDLRKRLCRNHPDTRTRACFTQWLCHLH-NEVNRKLGKPDFDCSKVDERWRDGWKDGSCD. This was attached via a FLAG tag (DYKDDDDK—Sequence ID No. 17) at its N-terminal to a secretion leader of Sequence ID No.2. The protein sequence of this fusion protein, including the leader is shown in Sequence ID No.7.

Sequence ID No. 7

MKVSTAFLCLLLTVSAFSAQVLADYKDDDDKAAPGERGRFHGGNLF

FLPGGARSEMMDDLATDARGRGAGRRDAAASASTPAQAPTSDSPVA

EDASRRRPCRACVDFKTWMRTQQKRDTKFREDCPPDREELGRHSWA

VLHTLAAYYPDLPTPEQQQDMAQFIHLFSKFYPCEECAEDLRKRLC

RNHPDTRTRACFTQWLCHLHNEVNRKLGKPDFDCSKVDERWRDGWK

DGSCD

A gene encoding Sequence ID No.7 was synthesised with the sequence Sequence ID No.8, consisting of *Escherichia coli* Lac promoter without an operator sequence, and an ALRP gene codon optimised for expression in *Escherichia coli*. This was cloned as an EcoRV Fragment into the HpaI site of NBJ078-18-3 to make pAVE0354 and confirmed by restriction digest and sequencing.

Sequence ID No. 8

GATATCACGCGTTTAGGCACCCCAGGCTTTACACTTTATGCTTCCG

GCTGGTATGTTGTGTGGACTTTAAGAAGGAGATATACATATGAAAG

TGAGCACCGCATTCTTGTGTCTGCTGTTGACGGTCTCCGCGTTCAG

CGCACAAGTTTTGGCGGACTATAAGGATGACGATGACAAAGCGGCA

CCGGGCGAACGCGGTCGTTTCCACGGTGGCAATTTGTTTTTCCTGC

CGGGCGGCGCCCGCAGCGAGATGATGGACGACTTGGCGACTGACGC

GCGTGGTCGTGGTGCTGGTCGTCGTGATGCAGCGGCCTCGGCAAGC

ACGCCGGCTCAGGCCCCAACCTCCGATAGCCCGGTGGCGGAGGACG

CTAGCCGCCGTCGCCCGTGTCGTGCGTGTGTTGACTTTAAAACCTG

GATGCGTACCCAACAGAAGCGTGACACCAAGTTTCGCGAAGACTGC

CCGCCGGACCGTGAGGAACTGGGTCGCCACTCTTGGGCGGTCCTGC

ACACGCTGGCGGCGTACTACCCGGATCTGCCTACGCCGGAACAGCA

GCAGGATATGCGCAATTCATCCATCTGTTTAGCAAGTTTTATCCT

TGCGAGGAGTGTGCCGAAGATTTGCGTAAGCGCCTGTGTCGTAACC

ATCCGGACACCCGTACCCGTGCCTGCTTTACCCAATGGTTGTGCCA

CCTGCACAATGAAGTTAACCGCAAATTGGGCAAACCGGATTTCGAC

TGCAGCAAAGTGGATGAGCGTTGGCGTGATGGTTGGAAGGATGGTA

GCTGCGATTAATGAATTATATTACTAATTAATTGGGGACCCTAGAG

GTCCCCTTTTTTATTTTAAAACTCGAGGATATC

Construction of CLD331 & CLD420

The starting vector for the generation of pAVE314 was pAVE029, prepared as described in WO2007/088371. The gene for IGF-1 with an LamB leader was synthesised as an NdeI/XhoI fragment, see Sequence ID No.9 below. This was cloned into pAVE029 NdeI/XhoI sites. Initial screening was by restriction digest of plasmid DNA. The sequence was then confirmed by sequencing. The resultant plasmid was named pAVE314.

Expression plasmid pAVE314 was transformed into *E coil* strain W3110 to make CLD331. Expression plasmid pAVE354 was then transformed into CLD331 make CLD420. The resultant recombinant strains were purified and maintained in glycerol stocks at −80° C.

Sequence ID No. 9

CATATGATGATTACCCTGCGTAAACTGCCGCTGGCAGTCGCAGTTG

CAGCCGGTGTTATGAGCGCACAGGCAATGGCAGGTCCGGAAACCCT

GTGTGGTGCAGAACTGGTTGATGCACTGCAGTTTGTTTGTGGTGAT

CGTGGCTTTTATTTTAATAAACCGACCGGTTATGGTAGCAGCAGCC

GTCGTGCACGTCAGACCGGTATTGTTGATGAATGTTGCTTTCGTAG

CTGTGATCTGCGTCGTCTGGAAATGTATTGTGCACCGCTGAAACCG

GCAAAAGCGCATAATAACTCGAG

Construction of CLD429 & CLD433

The starting vector for the generation of pAVE356 was pAVE029. The gene for human Growth Hormone (hGH) with an OmpA leader was synthesised as an NdeI/XhoI fragment, see Sequence ID No.10 below. This was cloned into pAVE029 NdeI/Xhol sites. Initial screening was by restriction digest of plasmid DNA. The sequence was then confirmed by sequencing. The resultant plasmid was named pAVE356.

Sequence ID No. 10

CATATGAAAAAGACTGCTATTGCTATTGCGGTTGCTCTGGCTGGTT

TCGCCACCGTGGCGCAGGCATTCCCGACGATTCCGCTGTCTCGTCT

GTTCGATAACGCTATGCTGCGTGCACATCGTCTGCACCAGCTGGCA

TTCGACACTTATCAAGAATTCGAGGAGGCCTACATCCCGAAAGAAC

AGAAATACAGCTTCCTGCAGAACCCGCAAACCTCCCTGTGCTTCAG

CGAATCCATCCCGACTCCGTCTAACCGCGAAGAAACCCAGCAGAAA

TCTAATCTGGAACTGCTGCGTATTAGCCTGCTGCTGATCCAGTCTT

GGCTGGAACCGGTGCAATTCCTGCGCAGCGTCTTCGCGAACTCCCT

GGTATATGGCGCTTCCGACTCTAACGTATACGATCTGCTGAAAGAC

CTGGAGGAGGGTATCCAGACCCTGATGGGCCGCCTGGAGGACGGCA

GCCCGCGTACTGGCCAGATCTTTAAACAGACTTACTCTAAATTCGA

CACCAACTCCCATAATGATGACGCCCTGCTGAAAAACTATGGTCTG

CTGTACTGCTTCCGTAAAGACATGGACAAAGTTGAGACCTTCCTGC

GTATTGTTCAGTGTCGCTCTGTTGAGGGTTCTTGCGGCTTCTAATG

ACTCGAG

Expression plasmid pAVE356 was transformed into W3110 to make CLD429. Expression plasmid pAVE354 was then transformed into CLD429 to make CLD433. The resultant recombinant strains were purified and maintained in glycerol stocks at −80° C.

Construction of CLD048 & CLD426

Strain CLD048 was prepared as described in WO 2007/088371.

Expression plasmid pAVE354 was then transformed into CLD048 to make CLD426. The resultant recombinant strains were purified and maintained in glycerol stocks at −80° C.

Construction of CLD430 & CLD428

The starting vector for the generation of pAVE157 is pAVE029. The gene for A5B7 Fab was synthesised as a NdeI/XhoI fragment, see Sequence ID No.11 below. This was cloned into pAVE029 NdeI/XhoI sites. Initial screening was by restriction digest of plasmid DNA. The sequence was then confirmed by sequencing. The resultant plasmid was named pAVE157.

Sequence ID No. 11
```
CATATGAAGAAGACTGCTATTGCTATTGCGGTTGCACTGGCTGGTT
TCGCTACCGTGGCGCAGGCACAGGTTCAGCTGCAGGAAAGCGGCGG
TGGTCTGGTTCAGCCAGGCGGTAGCCTGCGTCTGTCCTGCGCTACC
AGCGGTTTCACTTTTACCGACTACTACATGAACTGGGTGCGTCAGC
CGCCAGGCAAAGCGCTGGAATGGCTGGGCTTCATCGGTAACAAAGC
TAACGGCTACACTACCGAGTACTCCGCATCTGTAAAAGGTCGTTTT
ACCATCTCTCGTGACAAAAGCCAGTCTATCCTGTACCTGCAGATGA
ATACCCTGCGCGCTGAAGACTCCGCGACTTATTACTGTACCCGTGA
CCGTGGTCTGCGTTTTTACTTCGACTACTGGGGTCAGGGTACCACT
GTAACGGTCAGCTCCGCCTCCACTAAAGGCCCGAGCGTATTTCCTC
TGGCGCCGTCCTCCAAGTCCACTAGCGGCGGCACCGCAGCTCTGGG
CTGTCTGGTTAAAGACTACTTCCCAGAGCCGGTGACCGTTTCCTGG
AACAGCGGTGCACTGACCAGCGGCGTTCACACGTTTCCGGCCGTGC
TGCAATCCTCCGGTCTGTACTCTCTGTCTTCCGTCGTCACCGTTCC
GTCTAGCTCTCTGGGCACTCAGACCTATATCTGCAACGTCAATCAC
AACCCGTCTAACACCAAAGTTGACAAGAAAGTGGAGCCGAAATCTT
GCGATAAAACGCACACCTAATAACTGGCCCTGAGCTCCAAGTTCTA
CTTTAAAGAAACGGTTATCATGAAAAAGACCGCCATCGCTATCGCT
GTTGCGCTGGCAGGCTTTGCTACGGTTGCTCAAGCTGACATCGAAC
TGTCTCAGTCTCCGGCGATCCTGTCCGCGTCTCCAGGCGAAAAAGT
AACTATGACCTGTCGCGCTAGCTCTTCCGTTACCTACATCCACTGG
TATCAGCAGAAACCGGGTTCTTCCCCGAAAAGCTGGATCTACGCAA
CCTCCAACCTGGCTTCCGGCGTTCCGGCTCGTTTTTCTGGTTCTGG
CTCTGGCACGTCCTATTCTCTGACCATCAGCCGTGTAGAGGCAGAA
GACGCAGCTACCTATTACTGCCAGCACTGGTCCTCCAAACCTCCGA
CTTTCGGTGGCGGCACCAAACTGGAAATCAAGCGTACCGTCGCCGC
TCCGTCTGTTTTCATTTTCCCGCCGTCCGACGAGCAGCTGAAATCC
GGTACCGCCAGCGTAGTGTGCCTGCTGAACAACTTCTACCCACGTG
AGGCTAAAGTTCAGTGGAAAGTGGACAATGCCCTGCAGAGCGGCAA
CTCCCAGGAATCCGTTACCGAACAGGACAGCAAAGATTCCACTTAT
TCCCTGTCTTCCACTCTGACTCTGAGCAAAGCAGATTACGAGAAGC
ATAAGGTGTACGCCTGTGAAGTGACTCACCAGGGTCTGTCCTCTCC
GGTTACGAAAAGCTTTAACCGTGGCGAGTGCTAATAAGGATCCAGC
TCGAATTCCATCGATGATATCAGATCTCTCGAG
```

Expression plasmid pAVE157 was transformed into W3110 to make CLD430. Expression plasmid pAVE354 was then transformed into CLD430 to make CLD428. The resultant recombinant strains were purified and maintained in glycerol stocks at −80° C.

Construction of CLD453 & CLD454

The starting vector for the generation of pAVE366 was pAVE029. The gene for FGF21 with an OmpA leader was synthesised as an NdeI/XhoI fragment, see Sequence ID No.12 below. This was cloned into pAVE029 NdeI/XhoI sites. Initial screening was by restriction digest of plasmid DNA. The sequence was then confirmed by sequencing. The resultant plasmid was named pAVE366.

Sequence ID No. 12
```
CATATGAAAAAAACCGCTATTGCAATTGCAGTTGCACTGGCAGGTT
TTGCAACCGTTGCACAGGCACATCCGATTCCGGATAGCAGTCCGCT
GCTGCAGTTTGGTGGTCAGGTTCGTCAGCGTTATCTGTATACCGAT
GATGCACAGCAGACCGAAGCACATCTGGAAATTCGTGAAGATGGCA
CCGTTGGTGGTGCAGCAGATCAGAGTCCGGAAAGCCTGCTGCAGCT
GAAAGCACTGAAACCGGGTGTTATTCAGATTCTGGGTGTTAAAACC
AGCCGTTTTCTGTGTCAGCGTCCGGATGGTGCACTGTATGGTAGCC
TGCATTTTGATCCGGAAGCATGTAGCTTTCGTGAACTGCTGCTGGA
AGATGGTTATAATGTTTATCAGAGCGAACATCATGGTCTGCCACTG
CATCTGCCTGGTAATAAAAGTCCGCATCGTGATCCGGCACCGCGTG
GTCCGGCACGTTTTCTGCCGCTGCCTGGTCTGCCTCCTGCACTGCC
GGAACCTCCGGGTATTCTGGCACCGCAGCCTCCGGATGTTGGTAGC
AGCGATCCGCTGAGCATGGTTGGTCCGAGCCAGGGTCGTAGCCCGA
GCTATGCAAGCTAATAACTCGAG
```

Expression plasmid pAVE366 was transformed into W3110 to make CLD453. Expression plasmid pAVE354 was then transformed into CLD453 to make CLD454. The resultant recombinant strains were purified and maintained in glycerol stocks at −80° C.

Construction of CLD442 & CLD443

The starting vector for the generation of pAVE364 was pAVE029. The gene for RapLR with an OmpA leader was synthesised as an NdeI/XhoI fragment. This was cloned into pAVE029 NdeI/XhoI sites. Initial screening was by restriction digest of plasmid DNA. The sequence was then confirmed by sequencing. The resultant plasmid was named pAVE364.

Expression plasmid pAVE364 was transformed into W3110 to make CLD442. Expression plasmid pAVE354 was then transformed into CLD442 to make CLD443. The resultant recombinant strains were purified and maintained in glycerol stocks at −80° C.

RapLR Sequence
(Sequence ID No. 13)
```
GAAGGCCGTCAAGGCCACGTGTCTTGTCCAGGTACCATATGAAAAA
AACCGCCATTGCAATTGCAGTTGCTCTGGCAGGTTTTGCAACCGTT
GCACAGGCACAGGATTGGCTGACCTTTCAGAAAAAACATCTGACCA
ATACCCGTGATGTGGATTGCAATAATATTATGAGCACCAACCTGTT
TCATTGCAAAGATAAAAATACCTTTATTTATAGCCGTCCGGAACCG
GTTAAAGCAATTTGTAAAGGTATTATTGCCAGCAAAAATGTGCTGA
CCACGAGCGAGTTTTATCTGAGCGATTGTAATGTTACCAGCCGTCC
```

```
GTGTAAATATAAACTGAAAAAAAGCACCAATACCTTTTGCGTGACC

TGTGAAAATCAGGCACCGGTTCATTTTGTTGGTGTTGGTCATTGTG

AACAGAAACTGATTAGCGAAGAAGATCTGTAATAACTCGAGCTCTG

GAGCACAAGACTGGCCTCATGGGCCTTC
```

Construction of CLD438 & CLD439

The starting vector for the generation of pAVE362 was pAVE029. The gene for Elafin with an OmpA leader was synthesised as an NdeI/XhoI fragment, see Sequence ID No.14 below. This was cloned into pAVE029 NdeI/XhoI sites. Initial screening was by restriction digest of plasmid DNA. The sequence was then confirmed by sequencing. The resultant plasmid was named pAVE362.

```
                                       Sequence ID No. 14
CATATGAAAAAAACCGCCATTGCAATTGCAGTTGCTCTGGCAGGTT

TTGCAACCGTTGCACAGGCAGCACAGGAACCGGTTAAAGGTCCGGT

TAGCACCAAACCGGGTAGCTGTCCGATTATTCTGATTCGTTGTGCA

ATGCTGAATCCTCCGAATCGTTGTCTGAAAGATACCGATTGTCCGG

GTATTAAAAAATGTTGTGAAGGTAGCTGTGGCATGGCATGTTTTGT

TCCGCAGGAACAGAAACTGATTAGCGAAGAAGATCTGTAATAACTC

GAG
```

Expression plasmid pAVE362 was transformed into W3110 to make CLD438. Expression plasmid pAVE354 was then transformed into CLD438 to make CLD439. The resultant recombinant strains were purified and maintained in glycerol stocks at −80° C.

Construction of CLD440 & CLD441

The starting vector for the generation of pAVE363 was pAVE029. The gene for MIC6 with an OmpA leader was synthesised as an NdeI/XhoI fragment, see Sequence ID No.15 below. This was cloned into pAVE029 NdeI/XhoI sites. Initial screening was by restriction digest of plasmid DNA. The sequence was then confirmed by sequencing. The resultant plasmid was named pAVE363.

```
                                       Sequence ID No. 15
CATATGAAAAAAACCGCCATTGCAATTGCAGTTGCTCTGGCAGGTT

TTGCAACCGTTGCACAGGCACGTCTGTTTCGTTGTTGTGCAGCAGC

AGTTGTTGCAGCAGAAAGCCTGCTGTGGCTGAAAAATGGTAGCCCG

TTTTTTGCATTTCTGCCTGGTAATGGTGAAATTGCAGATAATTGTA

GCGGTAATCCGTGTGGTGGCACCGCAGCAGGCACCTGTATTAATAC

CCCGAGCGGTTATGATTGTCGTTGTGAACCGGGTTATGTTCTGGGT

GTTGAAAATGATCAGGTTACCTGTATGATGCCGAGCGGTGTTCCGA

TGGCAAATTTTGTTCAGCTGAGCGAAAAACCGGCAGCATGTAGCAG

CAATCCGTGCGGTCCGGAAGCAGCAGGTACATGTAATGAAACCAAT

AGCGGTTATATTTGCCGTTGCAATCAGGGTTATCGTATTAGCCTGG

ATGGCACCGGTAATGTTACCTGTATTGTTCGTCAGGAAAGCGGTTG

CGAAGAAATGGTTGTGGTCCGCCGGATGCCGTTCAGAGCTGTCGT

CGTCTGACCGGCACAGCAGGTCGTCTGTGTGTTTGTAAAGAAATT
```

```
TTATTGCCACCATTGATGCCAGCGCACATATTACCTGTAAACGTGT

TCCGCCGCATTATCGTAAACCGCCGTTTGAATTTGGTAAAGGTGGT

CATCCGGTTGATAGCGAACCGAGCAAACGTCAGCGTGAAGATGAAG

GTGAAAGCCGTGAACCGGAAAGCGATAGCACCGAACCGGGTCGTGA

TCAGGAACGTCGTACACCGCTGGAAGAAAGCCAGGAACCGGAAGGT

AGCACACCGGATAGCCAGCAGAGCCGTGGTGGTAGCGGTAGCGATA

GTACCGAAAGCGAAGAACAGGGTAAAGAACGTGAAGAAGGTAGCGG

TCACGCCGGTGCAATTGCCGGTGGTGTTATTGGTGGTCTGCTGCTG

CTGAGCGCAGCCGGTGCCGGTGTTGCATATATGCGTAAAAGCGGTA

GCGGTGGTGGTGAAGAAATTGAATATGAACGTGGTATTGAAGCAGC

AGAAGCAAGCGAAGTTGAAGTTCTGGTTGATCTGGATAGCAAAACC

TGGGATGAACAGAAACTGATTAGCGAAGAAGATCTGTAATAACTCG

AG
```

Expression plasmid pAVE363 was transformed into W3110 to make CLD440. Expression plasmid pAVE354 was then transformed into CLD440 to make CLD441. The resultant recombinant strains were purified and maintained in glycerol stocks at −80° C.

Shake-Flask Evaluation

10 μl of the thawed glycerol stock was inoculated into 5 ml Luria Broth (LB, 5 g/L yeast extract, 10 g/L tryptone, and 5 g/L sodium chloride) supplemented with tetracycline (10 μg/ml). This was incubated at 37° C. in an orbital shaker for 16 h. 500 μl of this culture was then used to inoculate 250 ml Erlenmeyer flasks containing 50 ml of Luria Broth (composition as described above). The flasks were incubated at 37° C., at 200 rpm in an orbital shaker. Growth was monitored until OD600.0.5+/−0.1. At this point flasks were induced with an appropriate concentration of IPTG (isopropyl-β-D-1-thiogalactopyranoside) and the incubation continued, under the conditions described above for 22 hours, during which samples were taken for measurement of growth, and accumulation of product.

Fermentation Evaluation

Fermentation inocula for the strains as noted in Results below were raised by adding 450 μl of glycerol stock to a 2.0 L baffled shake flask containing 450 mL of Luria Broth (LB) containing 5 g/L yeast extract, 10 g/L peptone, 10 g/L sodium chloride, 10 g/L glucose and 15 mg/L tetracycline. Chloramphenicol was not added when cultivating strains without foldases but included at a concentration of 34 mg/L when cultivating strains with foldases. Inocula were grown for 10 h at 37° C. in a shaker-incubator with an agitation of 200 rpm. 20 ml of shake flask inoculum was used to inoculate a 5 L working volume fermenter containing 4 L of minimal glycerol batch growth medium supplemented with yeast extract and tetracycline when cultivating strains without foldases or yeast extract, tetracycline and chloramphenicol when cultivating strains with foldases. The fermentation was carried out under the operating conditions described below. Temperature was controlled either at a constant temperature of 30° C. (IGF-1 strains) or at 37° C. for the first 7-9 hours then reduced to 30° C. and controlled at 30° C. for the remainder of the fermentation (all others). pH was controlled at 7.0 by automatic addition of 25% (w/v) ammonium hydroxide. The dissolved oxygen tension (dOT) set point was 30% of air saturation and was controlled by automatic adjustment of the fermenter stirrer speed, from a minimum of 250 rpm up to a maximum of 1500 rpm, and supplementation of oxygen to the inlet gas stream. Airflow to the fermenter vessel was 0.5 v/v/min throughout.

Fermentations were performed in batch mode until depletion of the carbon source (i.e. glycerol) which was characterized by a sharp rise in dOT. Fed-batch fermentation was initiated at the point of carbon source exhaustion by the addition of a glycerol/ammonium sulphate feed. Induction was carried out by addition of IPTG to a final concentration of 2 mM (IGF-1) 0.1 mM (h-Gh) or 0.5 mM A5-B7 once the biomass level in the fermentation reached OD600=45-55. The fed-batch phase was continued for 40-48 h post induction (40 h for IGF-1 runs; 48 h the rest). The cells and residual cell free growth medium were then harvested. The harvested cells were further subjected to osmotic shock cell fractionation to isolate the cellular fraction containing proteins that had partitioned in the soluble E. coli periplasmic fraction.

Analytical Methods

The accumulation levels for Shake Flask and Fermentation evaluations were determined using SimplyBlue stained SDS-PAGE gels of whole cell lysates of the samples. The harvested cells were further subjected to osmotic shock cell fractionation to isolate the cellular fraction containing proteins that had partitioned in the soluble E coli periplasmic fraction and the accumulation level in different fractions determined using SimplyBlue stained SDS-PAGE gels. The OS1 (Osmotic Shock) fraction is the supernatant after washing in sucrose buffer, the OS2 fraction is the supernatant after washing with a low ionic strength buffer, the 'supernatant/growth' medium is the cell free residual growth medium and the 'cell pellet' is the cell pellet after osmotic shock fractionation.

The accumulation of biologically active D1.3 Fab in the soluble periplasmic extract and residual growth medium was estimated by determining the binding of D1.3 Fab to lysozyme (antigen) in an ELISA assay by reference to a standard curve prepared with purified active D1.3 Fab.

The accumulation of biologically active A5B7 Fab in the soluble periplasmic extract and residual growth medium was estimated by determining the binding of A5B7 Fab to an antibody specific for human IgG Fab domain in an ELISA assay by reference to a standard curve prepared with purified active D1.3 Fab.

Results

Strains CLD331 and 420

SDS-PAGE/Western blot showed that in shake-flasks IGF-1 was secreted as a processed product of ~6 kDa from both shake-flasks and fermentations indicating successful secretion.

Strains CLD429 and 433

SDS-PAGE showed that in shake-flasks hGH was secreted as a processed product of ~22 kDa indicating successful secretion.

Strains CLD048 and 433

ELISA analysis showed that in shake-flasks D1.3 was secreted at 600 µg/ml with foldases compared with 300 µg/ml without foldases, under equivalent conditions. This indicated that expression of the foldases could lead to an increase in the yield of active product.

Strains CLD428 and 430

ELISA analysis showed that in shake-flasks A5B7 was secreted at 54 ng/ml/OD with foldases compared with 18 ng/ml/OD without foldases, under equivalent conditions In fermenter A5B7 was secreted at 1335 µg/L with foldases compared with 874 µg/L without foldases.

These results indicated that expression of the foldases could lead to an increase in the yield of active product.

Strains CLD453 and 454

SDS-PAGE/Western blot showed that in shake-flasks FGF-21 was secreted as a processed product of ~23 kDa indicating successful secretion.

Strains CLD442 and 443

SDS-PAGE/Western blot showed that in shake-flasks RapLR1 was secreted as a processed product of ~12 kDa indicating successful secretion.

Strains CLD438 and 439

SDS-PAGE/Western blot showed that in shake-flasks Elafin was secreted as processed product of ~7 kDa, in the presence of foldases, but was not detectable in the strain without the foldases. This indicated that the expression of the foldases could lead to an increase in the secretion of product.

Strains CLD440 and 441

SDS-PAGE/Western blot showed that in shake-flasks MIC6 was secreted as a product of ~39 kDa indicating successful secretion.

The invention claimed is:

1. A process of producing a target recombinant polypeptide which comprises expressing, in a prokaryotic host cell, an expression cassette encoding the target polypeptide and a target polypeptide secretion leader effective to achieve secretion of the target polypeptide into the periplasm of the prokaryotic host cell, and co-expressing an expression cassette encoding a Mia40 family mitochondrial foldase and a mitochondrial foldase secretion leader effective to achieve secretion of the mitochondrial foldase into the periplasm of the prokaryotic host cell.

2. The process according to claim 1 further comprising co-expressing one or more additional mitochondrial foldases.

3. The process according to claim 2, wherein the additional mitochondrial foldases comprise an erv1 foldase or an erv2 foldase.

4. The process according to claim 1, wherein the expression cassette encoding the target polypeptide and the expression cassette encoding the mitochondrial foldase are located on different vectors.

5. The process according to claim 1, wherein the expression cassette encoding the target polypeptide and the expression cassette encoding the mitochondrial foldase are located on the same vector.

6. The process according to claim 1, wherein the mitochondrial foldase is expressed with a solubility fusion partner.

7. The process according to claim 1, wherein the prokaryotic host cell is a bacterial cell.

* * * * *